US007226603B2

(12) United States Patent
Murray

(10) Patent No.: US 7,226,603 B2
(45) Date of Patent: Jun. 5, 2007

(54) HBV CORE ANTIGEN PARTICLES WITH MULTIPLE IMMUNOGENIC COMPONENTS ATTACHED VIA PEPTIDE LIGANDS

(75) Inventor: Kenneth Murray, Edinburgh (GB)

(73) Assignee: Biogen Idec MA Inc., Cambridge, MA (US)

( * ) Notice: Subject to any disclaimer, the term of this patent is extended or adjusted under 35 U.S.C. 154(b) by 408 days.

(21) Appl. No.: 10/872,550

(22) Filed: Jun. 21, 2004

(65) Prior Publication Data

US 2004/0234554 A1 Nov. 25, 2004

Related U.S. Application Data

(60) Division of application No. 10/448,546, filed on May 29, 2003, now Pat. No. 6,827,937, which is a division of application No. 09/873,459, filed on Jun. 4, 2001, now Pat. No. 6,627,202, which is a continuation-in-part of application No. PCT/US99/28755, filed on Dec. 3, 1999.

(60) Provisional application No. 60/110,911, filed on Dec. 4, 1998.

(51) Int. Cl.
*A61K 39/29* (2006.01)

(52) U.S. Cl. ................................ 424/227.1; 424/194.1; 424/196.11; 424/197.11; 424/202.1; 424/204.1; 530/403; 530/806; 530/810; 435/5; 435/7.1; 435/7.92; 436/501

(58) Field of Classification Search ..................... 435/5, 435/7.1, 7.92; 436/501; 424/194.1, 196.11, 424/197.11, 227.1; 530/403
See application file for complete search history.

(56) References Cited

U.S. PATENT DOCUMENTS

| | | | | |
|---|---|---|---|---|
| 4,818,527 | A | 4/1989 | Thornton et al. | 424/88 |
| 5,204,096 | A | 4/1993 | Neurath et al. | 424/89 |
| 5,204,446 | A | 4/1993 | Kumazawa et al. | 530/325 |
| 5,378,814 | A | 1/1995 | Houghton et al. | 530/350 |
| 5,436,126 | A | 7/1995 | Wang | 435/5 |
| 5,512,648 | A | 4/1996 | Sparrow et al. | 526/307 |
| 5,531,990 | A | 7/1996 | Thanavala et al. | 424/131.1 |
| 5,547,669 | A | 8/1996 | Rogers et al. | 424/185.1 |
| 5,556,744 | A | 9/1996 | Weiner et al. | 435/5 |
| 5,965,140 | A | 10/1999 | Valenzuela et al. | 424/202.1 |

FOREIGN PATENT DOCUMENTS

| | | |
|---|---|---|
| EP | 0 271 302 A | 6/1988 |
| WO | WO 96/39502 | 12/1996 |
| WO | WO 98/18818 | 5/1998 |

OTHER PUBLICATIONS

B. Böttcher et al., "Determination of the Fold of the Core Protein of Hepatitis B Virus by Electron Cryomicroscopy", *Nature*, 386, pp. 88–91 (1997).

B. Böttcher et al., "Peptides that block hepatitis B virus assembly: analysis by cryomicroscopy, mutagenesis and transfection", *EMBO J.*, 17, pp. 6839–6845 (1998).

G.P. Borisova et al., "Recombinant Core Particles of Hepatitis B Virus Exposing Foreign Antigenic Determinants on their Surface", *FEBS Lett.*, 259, pp. 121–124 (1989).

G. Borisova et al., "Hybrid Hepatitis B Virus Nucleocapsid Bearing an Immunodominant Region from Hepatitis B Virus Surface Antigen", *J. Virol.*, 67, pp. 3696–3701 (1993).

V. Bruss et al., "The Role of Envelope Proteins in Hepatitis B Virus Assembly", *Proc. Natl. Acad. Sci.*, 88, pp. 1059–1063 (1991).

V. Bruss et al., "Post–translational Alteration in Transmembrane Topology of Hepatitis B Virus Large Envelope Protein", *EMBO J.*, 13, pp. 2273–2279 (1994).

N.C. Collier et al., "Inhibition of Influenza Virus Formation by a Peptide That Corresponds to Sequences in the Cytoplasmic Domain of the Hemagglutinin,", *Virology*, 183, pp. 769–772 (1991).

J.F. Conway et al., "Visualization of a 4–Helix Bundle in the Hepatitis B Virus Capsid by Cryo–electron Microscopy", *Nature*, 386, pp. 91–94 (1997).

J.F. Conway et al., "Hepatitis B Virus Capsid: Localization of the Putative Immunodominant Loop (Residues 78–83) on the Capsid Surface, and Implications for the Distinction between c and e–Antigens", *J. Mol. Biol.*, 279, pp. 1111–1121 (1998).

R.A. Crowther et al., "Three–Dimensional Structure of Hepatitis B Virus Core Particles Determined by Electron Microscopy", *Cell*, 77, pp. 943–950 (1994).

(Continued)

*Primary Examiner*—Jeffrey Stucker
*Assistant Examiner*—Bo Peng
(74) *Attorney, Agent, or Firm*—Fish & Neave IP Group Ropes & Gray LLP; Margaret A. Pierri; Nina R. Horan

(57) ABSTRACT

This invention relates to hepatitis B virus ("HBV") core antigen particles that are characterized by multiple immunogen specificities. More particularly, the invention relates to HBV core antigen particles comprising immunogens, epitopes, or other related structures, crosslinked thereto by ligands which are HBV capsid-binding peptides that selectively bind to HBV core protein. Such particles may be used as delivery systems for a diverse range of immunogenic epitopes, including the HBV capsid-binding peptides, which advantageously also inhibit and interfere with HBV viral assembly by blocking the interaction between HBV core protein and HBV surface proteins. Mixtures of different immunogens and/or capsid-binding peptide ligands may be crosslinked to the same HBV core particle. Such resulting multicomponent or multivalent HBV core particles may be advantageously used in therapeutic and prophylactic vaccines and compositions, as well as in diagnostic compositions and methods using them.

28 Claims, 2 Drawing Sheets

OTHER PUBLICATIONS

M.R. Dyson et al., "Direct Measurement via Phage Titre of the Dissociation Constants in Solution of Fusion Phage–Substrate Complexes", *Nucleic Acids Res.*, 23, pp. 1531–1535 (1995).

M.R. Dyson and K. Murray, "Selection of Peptide Inhibitors of Interactions Involved in Complex Protein Assemblies: Association of the Core and Surface Antigens of Hepatitis B Virus", *Proc. Natl. Acad. Sci. USA*, 92, pp. 2194–2198 (1995).

D.A. Fallows et al., "Hepadnaviruses: Current Models of RNA Encapsidation and Reverse Transcription", *Advances in Virus Research*, 46, pp. 165–194 (1996).

V. Germaschewski and K. Murray, "Screening a Monoclonal Antibody With a Fusion–Phage Display Library Shows a Discontinuity in a Linear Epitope Within PreS1 of Hepatitis B Virus", *J. Med. Virol.*, 45, pp. 300–305 (1995).

S.S. Hong et al., "Protein ligands of the human adenovirus type 2 outer capsid identified by biopanning of a phage–displayed peptide library on separate domains of wild–type and mutant penton capsomers", *EMBO J.*, 14, pp. 4714–4727 (1995).

B.B. Knowles et al., "Human Hepatocellular Carcinoma Cell Lines Secrete the Major Plasma Proteins and Hepatitis B Surface Antigen", *Science*, 209, pp. 497–499 (1980).

K. Murray et al., "The Core Antigen of Hepatitis B Virus as a Carrier For Immunogenic Peptides", *Bio. Chem.*, 380, pp. 277–283 (1999).

M. Nassal et al., "Tropological Analysis of the Hepatitis B Virus Core Particle by Cysteine–Cysteine Cross–linking", *J. Mol. Biol.*, 225, pp. 1013–1025 (1992).

A.R. Neurath et al., "Identification and Chemical Synthesis of a Host Cell Receptor Binding Site on Hepatitis B Virus", *Cell*, 46, pp. 429–436 (1986).

M. Pasek et al., "Hepatitis B Virus Genes and Their Expression in *E. coli", Nature*, 282, pp. 575–579 (1979).

P.C.N. Rensen et al., "Selective Liver Targeting of Antivirals by Recombinant Chylomicrons—A New Therapeutic Approach to Hepatitis B", *Nat. Med.*, 1, pp. 221–225 (1995).

J. Salfeld et al., "Antigenic Determinants and Functional Domains in Core Anitgen and E Antigen from Hepatitis B Virus", *J. Virol*, 63, pp. 798–808 (1989).

M. Sällberg et al., "Characterisation of a Linear Binding Site for a Monoclonal Antibody to Hepatitis B Core Antigen", *J. Med. Virol.*, 33, pp. 248–252 (1991).

F. Schödel et al., "The Position of Heterologous Eptiopes Inserted in Hepatitis B Virus Core Particles Determines Their Immunogenicity", *J. Virol.*, 66, pp. 106–114 (1992).

F. Schödel et al., "Hybrid hepatitis B virus core antigen as a vaccine carrier moiety: I. presentation of foreign epitopes", *J. of Biotechnol.*, 44, pp. 91–96 (1996).

J.K. Scott et al., "Searching for Peptide Ligands with an Epitope Library", *Science*, 249, pp. 386–390 (1990).

A.–L. Shiau and K. Murray, "Mutated Epitopes of Hepatitis B Surface Antigen Fused to the Core Antigen of the Virus Induce Antibodies that React with the Native Surface Antigen", *J. Med. Virol.*, 51, pp. 159–166 (1997).

S.J. Stahl and K. Murray, "Immunogenicity of Peptide Fusions to Hepatitis B Virus Core Antigen", *Proc. Natl. Acad. Sci. USA*, 86, pp. 6283–6287 (1989).

W.S. Tan et al., "Two Distinct Segments of the Hepatitis B Virus Surface Antigen Contribute Synergistically to its Association with the Viral Core Particles", *J. Mol. Biol.*, 286, pp. 797–808 (1999).

K. Ueda et al., "Three Envelope Proteins of Hepatitis B Virus: Large S, Middle S and Major S Proteins Needed for the Formation of Dane Particles", *J. Virol.*, 65, pp. 3521–3529 (1991).

R. Ulrich et al., "Core particles of hepatitis B virus as carrier for foreign epitopes", *Adv. Virus. Res.*, 50, pp. 141–182 (1998).

L. Weiss et al., "The HBV–Producing Cell Line HepG2–4A5: A New in vitro System for Studying the Regulation of HBV Replication and for Screening Anti–Hepatitis B Virus Drugs", *Virology*, 216, pp. 214–218 (1996).

A. Yoshikawa et al., "Chimeric Hepatitis B Virus Core Particles with Parts or Copies of the Hepatitis C Virus Core Protein", *J. Virol.*, 67, pp. 6064–6070 (1993).

J. Zheng et al., "The Structure of Hepadnaviral Core Antigens," *J. Biol. Chem.*, 267, pp. 9422–9429 (1992).

FIG. 2

CHARACTERISTICS OF VARIOUS HBcAg FUSION PROTEINS

| Peptide sequence[a] | Position[b] | Length[c] | Features | Reference |
|---|---|---|---|---|
| β-galactosidase (1-8) | N (3) | 192 | M, A, I | Stahl et al. 1982 |
| FMDV VPI (142-160) | N (pre-core) | 215 | A, I | Clarke et al. 1987 |
| HBV PreS1 | C (144) | 187; 198 | M, A, I | Stahl and Murray, 1989 |
| HBV PreS1 | C (144); 144/145 | 193-233 | A, I | Borisova et al. 1989 |
| HBV PreS1 | N; N (pre-core) | 210; 224 | A, I, T | Schödel et al. 1992 |
| HBV PreS2 | C (144) | 191 | A, I | Stahl and Murray, 1989 |
| HBV PreS2 | C (144); 144/145 | 199; 236 | A, I | Borisova et al. 1989 |
| HBV PreS2 | C (156) | 167 | A, I, T | Schödel et al. 1992 |
| HBV PreS1; PreS2 | 75/83; C (156) | 187 | A, I, T | Schödel et al. 1992 |
| HBV PreS1 + PreS2 | C (144) | 218 | M, A, I, T | Shiau 1993 |
| HBV $S_{111-156/165}$ | C (144) | 211; 218 | A, I | Stahl and Murray, 1989 |
| HBV $S_{111-156}$ (145 mutants) | C (144) | 211 | M, A, I, T | Shiau and Murray, 1997 |
| HBV $S_{111-149}$ | 78/82-144 | 180 | A, I | Borisova et al. 1993 |
| HBV PreS1 + PreS2 + $S_{111-156}$ | C (144) | 266 | M, A, I, T | Shiau 1993 |
| HBV $S_{111-156}$ + PreS1 + PreS2 + $S_{111-156}$[e] | C (144); N, C (144) | 318; 314 | M, A, I, T | Shiau 1993 |
| HIV Env (728-751) | C (144) | 178 | I | Stahl and Murray, 1989 |
| HIV gp 41 (78-129) | C (144); 144/145 | 196; 235 | A | Borisova et al. 1993 |
| BLV gp 51 (56-103) | C (144) | 192 | A | Borisova et al. 1993 |
| HCV HCc (several) | C (149) | 186-881 | M, A | Yoshikawa et al. 1993 |

a    Origin of the peptide(s) fused to HBcAg. Numbers in parenthesis refer to amino acid sequences. Several authors used a number of different segments of PreS1 and PreS2.
b    Position(s) of fusion in HBcAg: N, N-terminus; C, C-terminus, or truncated at the residue in parentheses. Internal fusions are indicated by a slash between two numbers.
c    Total number of amino acids in the fusion protein.
d    M, morphology (electron microscopy); A, antigenicity; I, antibody production; T, T-cell proliferation.
e    Some combinations included the additional $S_{111-156}$ segment in the order indicated, but in others, it was placed at the N-terminus of the HBcAg sequence.

HBV CORE ANTIGEN PARTICLES WITH MULTIPLE IMMUNOGENIC COMPONENTS ATTACHED VIA PEPTIDE LIGANDS

This application is a divisional of application Ser. No. 10/448,546, filed May 29, 2003 now U.S. Pat. No. 6,827,937, which is a divisional of application Ser. No. 09/873,459, filed Jun. 4, 2001, now U.S. Pat. No. 6,627,202, which is a continuation of PCT application number PCT/US99/28755, filed Dec. 3, 1999, which in turn claims the benefit of U.S. provisional application No. 60/110,911, filed Dec. 4, 1998.

TECHNICAL FIELD OF THE INVENTION

This invention relates to hepatitis B virus ("HBV") core antigen particles that are characterized by multiple immunogen specificities. More particularly, the invention relates to HBV core antigen particles comprising immunogens, epitopes, or other related structures, crosslinked thereto by ligands which are HBV capsid-binding peptides that selectively bind to HBV core protein. Such particles may be used as delivery systems for a diverse range of immunogenic epitopes, including the HBV capsid-binding peptides, which advantageously also inhibit and interfere with HBV viral assembly by blocking the interaction between HBV core protein and HBV surface proteins. Mixtures of different immunogens, HBV capsid-binding peptide ligands, or both, may be crosslinked to the same HBV core particle. Such resulting multicomponent or multivalent HBV core particles may be advantageously used in therapeutic and prophylactic vaccines and compositions, as well as in diagnostic compositions and methods using them.

BACKGROUND OF THE INVENTION

The front-line of clinical immunotherapeutic regimens includes patient immunizations against infectious pathogens and other health-threatening agents. Despite the plethora of immunization agents, inoculations may afford, at best, partial immunity, requiring frequent re-immunizations. Such is the case for various conventional monovalent or polyvalent vaccines. And even among such vaccines, the number of single agent inoculants capable of eliciting immunity against a variety of immunogens is limited. Furthermore, antigenic variation among pathogens may limit the efficacy of conventional vaccines.

Due to such obstacles, efforts have focused on methodologies for enhancing the immune system response to given immunogens. To that end, immunogenic conjugates have been produced by linking immunogens to hepatitis B virus ("HBV") core particles (also referred to as nucleocapsids or nucleocapsid shells), in efforts to enhance the immunogenicity of the linked immunogen, through the operation of T cell dependent and T cell independent determinants of HBV core antigen. See, for example, U.S. Pat. No. 4,818,527 and R. Ulrich et al., "Core Particles of Hepatitis B Virus as Carrier for Foreign Epitopes", *Adv. Virus. Res.*, 50, pp. 141–82 (1998). Enhanced immunogenicity of epitopes of interest has also been approached via hybrid viral particle-forming proteins, comprising at least a portion of a naturally occurring viral particle forming protein, for example HBV surface antigen, and one or more epitopic sites of interest. See U.S. Pat. No. 5,965,140. As evident from such efforts, proteins of HBV have been used as platforms for presenting immunogens of interest to the immune system.

Hepatitis B virus is a blood-borne virus, comprising a small, partially double-stranded DNA genome, carrying four extensively overlapping open reading frames, consisting of an inner nucleocapsid, comprising the HBV core protein ("HBcAg"), viral polymerase and viral DNA, surrounded by a membranous envelope containing HBV surface antigens ("HBsAg"). The viral envelope contains three different, but related surface antigen proteins, long (L), medium (M) and short (S), which share a common carboxy terminal region but have different amino termini, arising from variable use of initiation triplets at different points within a continuous open reading frame.

The long polypeptide (L polypeptide) consists of pre-S1, pre-S2 and S regions. It is the product of the entire reading frame and comprises the pre-S1 domain of 108 amino acids (or 199, depending on the virus subtype) at its amino terminus, followed by the pre-S2 domain of 55 amino acids, and the short polypeptide (S polypeptide) region of 226 amino acids. The medium-length polypeptide (M polypeptide) has the pre-S2 domain at its amino terminus followed by the S region, whereas the S polypeptide, which is the most abundant form, consists of only the S region. The pre-S regions are believed to play an important role in both viral assembly and attachment to the host cell. The S form is more abundant than the M and L forms of HBsAg in the virus, and occurs in both glycosylated and nonglycosylated forms [V. Bruss and D. Ganem, "The Role of Envelope Protein in Hepatitis B Virus Assembly", *Proc. Natl. Acad. Sci. USA*, 88, pp. 1059–63 (1991); V. Bruss et al., "Post-translational Alteration in Transmembrane Topology of Hepatitis B Virus Large Envelope Protein", *EMBO J.*, 13, pp. 2273–79 (1994); A. R. Neurath et al., "Identification and Chemical Synthesis of a Host Cell Receptor Binding Site on Hepatitis B Virus", *Cell*, 46, pp. 429–36 (1986); K. Ueda et al., "Three Envelope Proteins of Hepatitis B Virus: Large S, Middle S and Major S Proteins Needed for the Formation of Dane Particles", *J. Virol.*, 65, pp. 3521–29 (1991)]. Specific interactions between the outer surface of the core and the inner surface of the envelope are likely to guide correct assembly of the virus and stabilize the resulting particle HBV core protein can be expressed efficiently in *E. coli* [M. Pasek et al., "Hepatitis B Virus Genes and Their Expression in *E. coli*", *Nature*, 282, pp. 575–79 (1979)], where it assembles into icosahedral shells of two sizes containing either 180 (T=3) or 240 (T=4) subunits [R. A. Crowther et al., "Three-Dimensional Structure of Hepatitis B Virus Core Particles Determined by Electron Microscopy", *Cell*, 77, pp. 943–50 (1994)]. The subunits are clustered as dimers and each dimer forms a spike which protrudes on the surface of the shell. Using electron cryo-microscopy and image processing, a map of the T=4 shell was recently made at 7.4 Å resolution from images of more than 6000 individual particles [B. Böttcher et al., "Determination of the Fold of the Core Protein of Hepatitis B Virus by Electron Cryomicroscopy", *Nature*, 386, pp. 88–91 (1997)]. This revealed the fold of the polypeptide chain, which was largely α-helical and quite unlike previously solved viral capsids. Each dimer spike was formed by a pair of long α-helical hairpins, one from each monomer in the dimer [Böttcher et al. (1997); J. F. Conway et al., "Visualization of a 4-Helix Bundle in the Hepatitis B Virus Capsid by Cryo-electron Microscopy", *Nature*, 386, pp. 91–94 (1997)]. A numbering scheme which superimposed the amino acid sequence on the fold [Böttcher et al. (1997)] placed the major immunodominant region of the HBV core protein around amino acids 78–82 [J. Salfeld et al., "Antigenic Determinants and Functional Domains in Core Antigen and E Antigen from Hepatitis B Virus", *J. Virol*, 63, pp. 798–808 (1989); M. Sällberg et al., "Characterisation of a Linear Binding Site for a Monoclonal Antibody to Hepatitis B Core Antigen", *J. Med. Virol.*, 33, pp. 248–52 (1991)], at the tip of the spike.

Agents which inhibit HBV viral assembly include those that bind to the core antigen of HBV, thereby blocking the interaction between HBV core proteins and HBV surface proteins. Some such HBV capsid-binding peptides are described in PCT patent application WO98/18818 and in M. R. Dyson and K. Murray, "Selection of Peptide Inhibitors of Interactions Involved in Complex Protein Assemblies: Association of the Core and Surface Antigens of Hepatitis B Virus", *Proc. Natl. Acad. Sci. USA*, 92, pp. 2194–98 (1995).

As will be apparent from the disclosure to follow, HBV capsid-binding peptides may be advantageously used as ligands for constructing HBV core antigen particles characterized by the ability to elicit enhanced immune responses to single or multiple immunogens.

DISCLOSURE OF THE INVENTION

The present invention addresses the problems referred to above by providing HBV core antigen particles which elicit enhanced immunogenicity to one or more component immunogens. Such multicomponent or multivalent HBV core antigen particles comprise immunogens, epitopes, or other related structures, crosslinked thereto through ligands which are peptides that selectively bind to HBV core antigen particles, in addition to immunogenic domains or epitopes attached to or inserted into the HBV core antigen polypeptide via genetic manipulation of the coding sequence or by polypeptide synthesis. Such particles may be used as delivery systems for a diverse range of immunogenic epitopes, including the HBV capsid-binding peptides, which themselves, inhibit and interfere with HBV viral assembly by blocking the interaction between HBV core protein and HBV surface proteins. The resulting multicomponent or multivalent HBV core particles may be advantageously used in therapeutic and prophylactic vaccines and compositions, as well as diagnostic compositions and methods using them.

The present invention advantageously permits mixtures of different immunogens, HBV capsid-binding peptide ligands, or both, to be crosslinked to the same HBV core particle. The result is single particles that are efficient stimulants of T cells and which are immunologically multivalent. Thus, a single antigen-presenting cell can stimulate the proliferation of multiple B cell clones of differing specificity.

BRIEF DESCRIPTION OF THE DRAWINGS

FIG. 2 is a table summarizing various HBV core antigen fusion proteins which may also serve as the HBV core antigen particle to which various immunogens may be linked through HBV capsid-binding peptides.

DETAILED DESCRIPTION OF THE INVENTION

Figure 1:
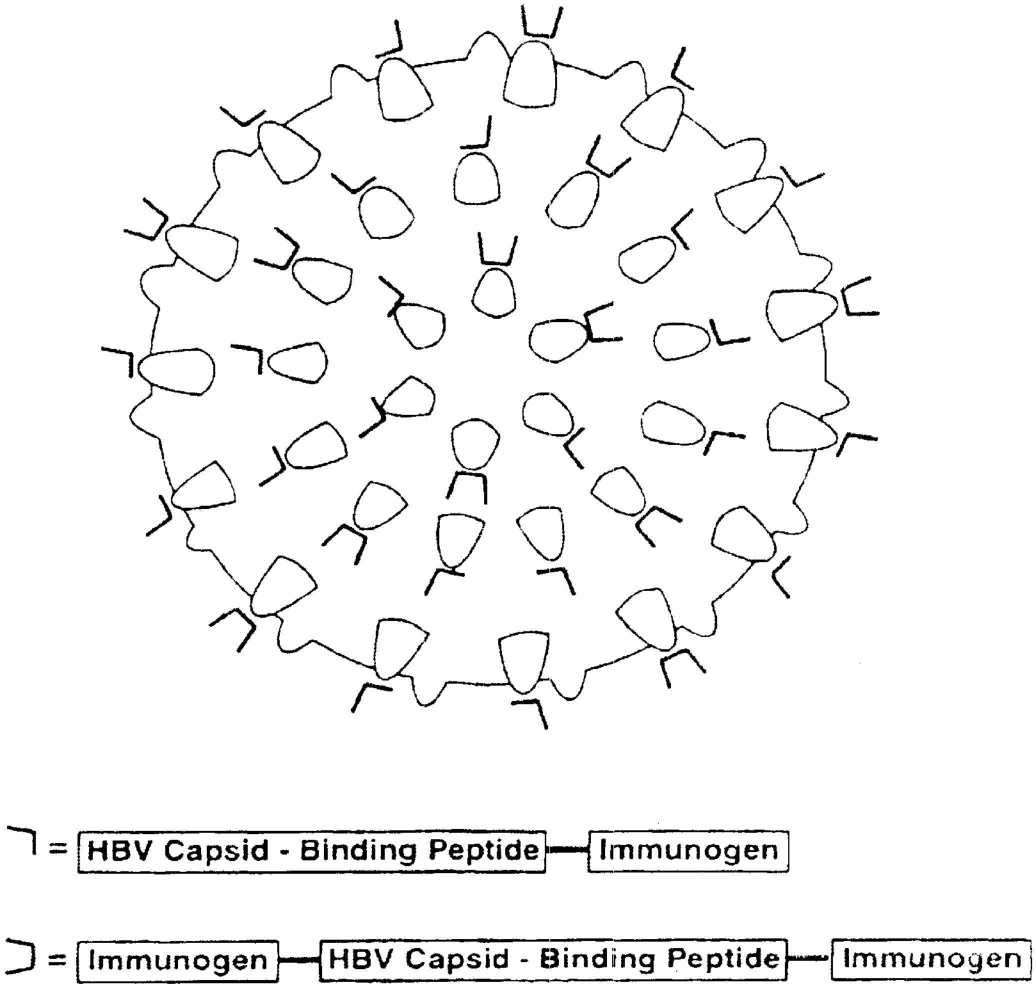
FIG. 1 depicts the structure of an HBV core antigen particle comprising various capsid binding immunogens. A "capsid binding immunogen" comprises at least one HBV capsid-binding peptide component and at least one immunogenic component. Each capsid binding immunogen is linked to the HBV core antigen particle through an HBV capsid-binding peptide.

In order that the invention herein described may be more fully understood, the following detailed description is set forth.

According to one embodiment of this invention, mixtures of more than one type of immunogen, and one or more types of HBV capsid-binding peptide ligands may be crosslinked to the same HBV core particle. Alternatively, multiple copies of the same immunogen may be linked to one type of HBV capsid-binding peptide and crosslinked to various positions on the HBV core particle. Multicomponent or multivalent HBV core antigen particles according to this invention are particularly useful for inducing antibodies to all component immunogens.

The use of HBV capsid-binding peptides to link immunogens to the HBV core antigen particle permits enhanced immunogen presentation, without destroying immunogenicity or stability of the immunogen by denaturation, conformational disruption or other destabilizing influences. For example, the HBV capsid-binding peptide linkers reduce the risk that component immunogens will interfere with each other to cause loss of functional material. As a result, the HBV core antigen particle elicits an enhanced immune response to its component immunogens. Therefore, it is possible to achieve desired therapeutic or prophylactic effects with fewer inoculations and/or less inoculant than that necessary, were each immunogen administered as a single-agent.

Linkage of immunogens to the HBV core antigen particle through HBV capsid-binding peptides also permits presentation of immunogens which vary in size, conformation and nature. As a result, the present invention allows inclusion in one vaccine or composition, combinations of immunogens useful to elicit a broad spectrum of immunity or treatment in a given individual.

Immunogens

Immunogens which may be linked to HBV capsid-binding peptides and thus, incorporated into HBV core antigen particles, include any molecule containing one or more immunologic, immunogenic or antigenic epitopes. Such epitopes may be linear, conformational, single, or mixed in nature.

More particularly, immunogens may be selected from any agent capable of eliciting an immune response. Such agents include, but are not limited to, antigens, antigenic determinants, proteins, glycoproteins, antibodies, antibody fragments, peptides, peptide mimotopes which mimic an antigen or antigenic determinant, polypeptides, glycopeptides, carbohydrates, oligosaccharides, polysaccharides, oligonucleotides and polynucleotides. Immunogens may also be allergens, toxins or endotoxins.

Such agents also include those targeted to or derived from various pathogenic agents, such as viruses, parasites, bacteria, fungi, phages, protozoa and plants. Such viruses include retroviruses, including human immunodeficiency type 1 and type 2 viruses and T cell leukemia virus; herpesviruses, such as herpes simplex type 1 and type 2 viruses, varicella-zoster viruses, cytomegaloviruses and Epstein-Barr virus, orthomyxoviruses, such as influenza A, influenza B and influenza C viruses; paramyxoviruses, such as respiratory syncytial virus, measles-like viruses, mumps virus and parainfluenza viruses; hepadnaviruses, such as hepatitis B viruses; flaviviruses, such as hepatitis C virus, hepatitis A virus, hepatitis E virus, yellow fever virus, dengue virus and tick-borne encephalitis viruses; picornaviruses, such as enteroviruses, rhinoviruses, foot and mouth disease viruses and poliomyelitis virus; togaviruses, such as rubella virus; rhabdovirus, such as rabies virus; adenoviruses, ebolaviruses; baculoviruses; hantaviruses; papovaviruses, such as papillomaviruses; parvoviruses; DNA viruses; RNA viruses; RNA tumor viruses, such as oncoviruses; and poxviruses, such as vaccinia virus. In addition, immunogens may be those which are targeted to or derived from bacillus, enterobacteria, clostridium, listeria, mycobacterium, pseudomonas, eubacteria, mycoplasma, chlamydia, spirochetes, neiseeria or salmonella. Immunogens may also be selected from the following epitopes of human immunodeficiency virus: GELDRWEKI (gag) (SEQ ID NO: 1); ELDKWAS (gp 40) (SEQ ID NO: 2); IGPGRAFYTTKN (V3 loop) (SEQ ID NO: 3); ELDKWA (gp 41) (SEQ ID NO: 4) and DRFYKTLRA (gp 41) (SEQ ID NO: 5).

Glycoproteins which may be linked to HBV capsid-binding peptides and thus, incorporated into HBV core antigen particles include, for example, antibodies, glycopeptides from or resembling surface components of animal cells or viruses or bacteria, such as those causing meningitis, or fragments of such moieties.

As will be appreciated by those of skill in the art, the size of the immunogen should not be large enough to allow a functional group thereof to interfere with the HBV capsid-binding peptide linker.

HBV Core Antigen Protein

Due to its particulate nature, HBV core antigen protein constitutes an advantageous platform for the presentation of multiple immunogens, of similar or dissimilar type, to the immune system. According to the present invention, this advantage is further enhanced by the use of HBV capsid-binding peptides as ligands to attach desired immunogens to the HBV core particle. Such particles contain either 90 or 120 ligand-binding sites—the capsid spikes, each composed of an HBV core antigen dimer (see FIG. 1). Thus, multiple immunogens may be physically linked to the HBV core antigen particle by the HBV capsid-binding peptides as ligands. The resulting particle is capable of inducing an immune response to all of its component immunogens.

HBV core antigen particles may be formed upon expression of recombinant coding sequences for HBV core antigen polypeptide in an appropriate microbial, animal or plant system. See, for example, Sambrook et al., *Molecular Cloning, A Laboratory Manual*, 2nd Edition, Cold Spring Harbor Press, Cold Spring Harbor, N.Y. (1989). The polypeptide to be expressed may comprise the full-length HBV core antigen sequence, or mutations, derivatives, truncations, or portions thereof, which retain the ability to assemble in particulate form in the cells of the expression system. Recombinant methods for producing such HBV core antigen particles are known in the art. See, for example, U.S. Pat. No. 4,710,463.

Alternatively, chemical synthesis methods may be used to produce HBV core antigen polypeptide. Based on the amino acid sequence of the HBV core antigen polypeptides, chemical synthesis may be carried out using solid phase synthesis [R. B. Merrifield, *Fed. Proced*., 21, p. 412 (1964); R. B. Merrifield, *Biochemistry*, 3, pp. 1385–90 (1964) and D. R. Milich et al., *J. Immunol*., 139, pp. 1223–31 (1987)].

Those skilled in the art will appreciate that since mutated or variant HBV core antigen sequences may influence reactions with binding or ligand peptides, the present invention applies equally to natural variants or mutations introduced by manipulation of coding sequences, or other procedures, in the HBV core antigen subunits or the corresponding binding or ligand peptides.

Mutation of Core Protein Residues Important for Peptide Binding

Methods used to determine the fold of the core protein have been applied to locate by cryomicroscopy the binding sites on the core protein of SLLGRMKGA (SEQ ID NO: 6), an HBV capsid-binding peptide that inhibits binding to L-HBsAg. This approach has now shown the peptide bound to the tips of the spikes, in both T=3 and T=4 shells. Image analysis shows that the peptide binding sites lie at the tip of the spikes which in the proposed numbering scheme for the polypeptide fold corresponds to residues in the region of amino acids 78–82. There are two acidic residues (glu77 and asp78) close to the tip of the core protein and the selected binding peptide contained two conserved basic residues. The importance of these oppositely charged residues in the binding reaction was confirmed when mutation of either of the acidic residues in the protein to alanine was found to greatly reduce the affinity of the peptides for the altered core shells. Changing aspartic acid 78 to alanine reduced the affinity 160-fold and changing glutamic acid 77 to alanine reduced the affinity 1000-fold. This suggests that either or both acidic residues on the HBV core antigen protein may provide at least part of the binding site for HBV capsid-binding peptides.

These results also illustrate the importance of the amino acid sequence of HBV core antigen in the region of the tip of the spike for ligand binding. Those of skill in the art will appreciate that HBV core antigen from some HBV strains may require mutation for effective binding of a particular ligand-immunogen peptide, or the selection and adaptation of variants of the ligand for effective binding to that specific HBV core antigen variant.

HBV Core Antigen Fusion Proteins

According to one embodiment of this invention, the HBV core antigen particle to which immunogens may be linked via HBV capsid-binding peptides may be one already displaying one or more immunogens, as a result of genetic fusion techniques. In one such technique, relevant coding sequences are incorporated at appropriate positions in plasmids or other vectors carrying that for HBV core antigen polypeptide.

Fusions to the β-galactosidase gene of *E. coli* used to enhance expression levels of HBV core antigen polypeptide demonstrated that replacement of the first two amino acids of the antigen with a sequence of eleven amino acids (eight from the amino terminus of β-galactosidase and three further residues resulting from translation of a linker sequence introduced in the gene fusion) had no adverse impact upon the ease of recovery, antigenicity, or morphology of the product [S. Stahl et al., "Hepatitis B Virus Core Antigen. Synthesis in *Escherichia Coli* and Application in Diagnosis", *Proc. Natl. Acad. Sci. USA*, 79, pp. 1606–10 (1982); B. J. Cohen and J. E. Richmond, "Electron Microscopy of Hepatitis B Core Antigen Synthesized in *E. Coli", Nature*, 296, pp. 677–78 (1982)].

HBV core antigen fusion proteins useful in the present invention may be produced as exemplified in S. J. Stahl and K. Murray, "Immunogenicity of Peptide Fusions to Hepatitis B Virus Core Antigen", *Proc. Natl. Acad. Sci. USA*, 86, pp. 6283–87 (1989). Alternatively, fusions of polypeptide sequences to the major segment of HBV core antigen to give highly immunogenic particles are exemplified with a number of viral coding sequences, as enumerated in FIG. 2. These include a particulate product with high immunogenicity, produced by expression via a vaccinia virus vector of the VP1 peptide (residues 142–160) fused through a heptapeptide linker sequence to the six amino acids of the pre-core sequence immediately preceding the amino terminus of HBV core antigen polypeptide [B. E. Clarke et al., "Improved Immunogenicity of a Peptide Epitope after Fusion to Hepatitis B Core Protein", *Nature*, 330, pp. 381–84 (1987)]. See also Ulrich et al. (1998) for other useful HBV core antigen fusion proteins.

A series of other fusion proteins are characterized by replacement of the arginine-rich region at the carboxy terminus of HBV core antigen polypeptide by other alternate coding sequences. Peptides that included the immunodominant a region of HBV surface antigen (residues 111–165), the pre-S1 and pre-S2 epitopes, and various segments of the envelope protein of human immunodeficiency virus (HIV) were attached to residue 144 of HBV core antigen polypeptide. All were expressed efficiently in *E. coli* to give particulate products displaying essentially the same morphology as that of HBV core antigen itself [Stahl and Murray, 1989]. The products displayed the antigenic reactivity of HBV core antigen and, like preparations of HBV core antigen polypeptide truncated at residue 144, those tested also exhibited HBV e antigen reactivity, whereas full-length HBV core antigen shows very little such activity. Fusion proteins carrying residues 111–156 or 111–165 from HBV surface antigen displayed no significant HBV surface antigen reactivity, a result not inconsistent with the conformation dependence of this major epitope, or the likelihood of the sequences being buried within the particles. Immunogenic responses to the fusion proteins, however, reflected their various component epitopes.

Immune responses to HBV surface antigen are complex, for in addition to epitopes residing in the pre-S1 and pre-S2 regions of L-HBsAg and the major immunodominant a region, a number of variable subtype determinants have been assigned to other regions of the short, or S polypeptide of HBV surface antigen [G. L. Le Bouvier, "The Heterogeneity of Australia Antigen", *J. Infect. Dis.*, 123, pp. 671–75 (1971); W. H. Bancroft et al., "Detection of Additional Antigenic Determinants of Hepatitis B Antigen", *J. Immunol.*, 109, pp. 842–48 (1972); A.-M. Couroucé-Pauty P. V. and Holland, "Summary of Workshop A2: HBsAg and its Subtypes", in *Viral Hepatitis*. G. N. Vyas, S. N. Cohen and R. Schmid, eds. (Philadelphia, USA: Franklin Institute Press), pp. 649–54 (1978)]. The HBV surface antigen coding sequences determined on HBV DNA cloned from sera of differing subtypes display differences in the corresponding protein sequences. However, specific single mutations of apparently critical residues did not effect a switch from one serological subtype (y) to another (d), but additional single mutations induced a gradual change with both y and d reactivities and immunogenicities being displayed from the same molecule [P. G. Ashton-Rickardt and K. Murray, "Mutations that Change the Immunological Subtype of Hepatitis B Virus Surface Antigen and Distinguish Between Antigenic and Immunogenic Determination", *J. Med. Virol.*, 29, pp. 204–14 (1989)]. The mutations involved were made within or close to the conformation-sensitive immunodominant a region, and were all within the segment of HBV core antigen used in the fusions to HBV core antigen described above.

The impact of the mutations upon the subtype specificity of the antibodies induced prompted the suggestion that fusion proteins might also provide a means for changing the specificity of the response to epitopes of interest, particularly if they are dependent on conformation. Mutations of glycine$_{145}$ to arginine, to mimic the natural escape mutant, and to other positively or negatively charged residues (lysine and glutamic acid) were therefore made at this residue in $HBcS_{111\text{-}156}$ for comparative studies of humoral and cellular immune responses [A. L. Shiau and K. Murray, "Mutated Epitopes of Hepatitis B Surface Antigen Fused to the Core Antigen of the Virus Induce Antibodies That React with the Nature Surface Antigen", *J. Med. Virol.*, 51, pp. 159–66 (1997)]. All were expressed efficiently in *E. coli*, yielding the anticipated particulate products showing strong HBV core antigenicity and all induced high titers of antibody to HBV core antigen in rabbits.

Like their parent protein $HBcS_{111\text{-}156}$, the three residue 145 mutants showed minimal interaction with antibody to HBV surface antigen in solid phase radio-immune assays (AUSRIA; Abbott Laboratories) or antibody precipitation assays in solution. However, they all showed strong reactions with a rabbit anti-HBV surface serum in immunoblotting experiments after electrophoresis in acylamide gels under denaturing conditions [A. L. Shiau, "Immunological Aspects of Hepatitis B Virus Core Antigen and its Derivatives", PhD Thesis, University of Edinburgh, UK. (1993)]. At high concentrations, the parent and mutant proteins also gave weakly positive reactions with antibody to HBV surface antigen when captured on a solid phase coated with antibody to HBV core antigen, possibly as a result of some disruption of the particles affording access for anti-HBsAg molecules [Shiau and Murray, 1997].

Immunized rabbits were used to examine T-cell responses to the fusion proteins, as well as antibody production. Peripheral blood mononuclear cells (PBMC) taken at various times after immunization were used for proliferation assays based upon [$^3$H]-thymidine incorporation in response to exposure to the HBV core antigen, or fusion protein used for immunization. In all cases, strong responses were found, with the fusion protein exhibiting a higher stimulation index than HBV core antigen, and HBV surface antigen being a poor stimulant, as expected. A double antibody radioimmunoprecipitation assay [C. J. Burrell et al., "Rapid Detection of Hepatitis B Surface Antigen by Double Antibody Radioimmunoassay", *J. Med. Virol.*, 3, pp. 1926 (1978)] with [$^{125}$I]-HBV surface antigen was used to measure anti-HBs in the serum samples and showed the anticipated positive response to $HBcS_{111\text{-}156}$. The arginine mutant also gave a positive response in this assay, although somewhat less than that of its parent molecule, and a weak response was obtained from the glutamic acid mutant, but none from the lysine mutant. Thus, the results showed that the fusion protein (designated $HBcS_{145R}$) carrying the arginine 145 mutant was a strong T-cell stimulant and induced antibodies with a broader reaction specificity.

A further group of fusions of various portions of the HBV surface antigen polypeptide, including residue 145 mutants, to HBV core antigen polypeptide was made to explore the effect of the overall size and the number and position of the various additional components on the immunogenicity of the products [Shiau (1993)]. These constructs are included in FIG. 2 and, as with the other fusions, all gave particulate products displaying the morphology of HBV core antigen, although fusions with the $HBs_{111\text{-}156}$ fragment at the amino terminus of HBV core antigen were less satisfactory, giving products that formed insoluble aggregates.

This group of products, like the earlier ones with the $HBcS_{111\text{-}156}$ segments, showed little or no reaction with antibody to HBV surface antigen on solid phase or in solution, but when captured by antibody to HBV core antigen on solid phase, they showed similar reactivity with antibody to HBV surface antigen and this was somewhat higher (about two-fold), with fusions carrying pre-S1 and pre-S2 segments in addition to $HBcS_{111\text{-}156}$. The stimulation indices for lymphocyte proliferation inhibition were again strong for all the fusion proteins and those that included pre-S segments as well as native or mutant $HBcS_{111\text{-}156}$ sequences gave the stronger responses. Inclusion of the pre-S1 and pre-S2 sequences between $HBc_{144}$ and the $HBcS_{111\text{-}156}$ sequences (either wild type or mutant) gave higher antibody levels in the double antibody radioimmunoprecipitation assay than the fusions lacking the pre-S segments, but the introduction of a second $HBcS_{111\text{-}}$ 156 sequence between $HBc_{144}$ and the pre-S sequences produced no further enhancement in any of the responses. The longest of these sequences attached to HBV core antigen polypeptide at $proline_{144}$—165 amino acids—had no obviously adverse impact on the yield or physical properties of the fusion protein.

The core protein (HCc) of hepatitis C virus (HCV) has also been fused, in part and in multiple full-length copies, to HBV core antigen polypeptide truncated at valine 149 [A. Yoshikawa et al., "Chimeric Hepatitis B Virus Core Particles with Parts of Copies of the Hepatitis C Virus Core Protein", *J. Virol.*, 67, pp. 6064–70 (1993)]. Fusions carrying HCc residues 39–75 showed negligible HCc antigenicity, but residues 1–91 or the full sequence of 180 amino acids gave positive reactions and the antigenicity increased almost arithmetically with the addition of further copies (up to four) of the 1–180 sequence via short linkers. Electronmicroscopy showed that the fusion carrying a single copy of HCc residues 1–91 formed particles morphologically equivalent to HBV core antigen polypeptide, but three full-length HCc copies greatly distorted this structure and the product was very sensitive to proteolysis giving, however, material that retained HBV core antigenicity. While the largest fusion protein carried more than 720 additional amino acids, the limit for a particle of the HBV core antigen type appears to be appreciatively less.

PreS sequences have been used in other studies of the effect of the position of fusion to HBcAg on immunogenicity. Borisova et al. (1989) made fusions with segments of pre-S1 (residues 20–68, 20–69, or 69–106) or the whole of pre-S2 linked to HBV core antigen truncated at proline 144 or inserted at this position within the full length HBV core antigen sequence. In these and analogous constructions with residues 56–103 of the envelope protein of bovine leukaemic virus (BLV) or residues 78–129 of the HIV transmembrane protein (gp41), the sequences fused to HBV core antigen were believed to be exposed on the particle surfaces, for all were reported to be both antigenic and immunogenic and the C-terminal arginine-rich domain apparently had little adverse effect.

F. Schödel et al., "The Position of Heterologous Epitopes Inserted in Hepatitis B Virus Core Particles Determines Their Immunogenicity", *J. Virol.*, 6, pp. 106–14 (1992) explored the impact of position of fusion on antigenicity and the immune response in inbred mice, when pre-S1 or pre-S2 segments were attached at the amino terminus of full-length HBV core antigen (either directly or via part of the pre-core sequence) or the carboxy terminus of truncated HBV core antigen; a further construction carried a pre-S1 segment between HBV core antigen residues 75 and 83 as well as the pre-S2 fragment at the truncated carboxy terminus (proline 156).

The comprehensive analysis showed that the pre-S1 sequence fused to the amino terminus of HBV core antigen via the short pre-core sequence was antigenic, but that fused directly to the amino terminus was not and, while both had the same HBV core antigen immunogenicity, the fusion via the pre-core sequence stimulated a much higher anti-pre-S1 response. The pre-S2 sequence at the truncated HBV core antigen terminus was antigenic and immunogenic to a similar degree in both contexts, but the pre-S1 sequence fused internally so as to replace residues 76–82 (which include the major HBV core antigen epitope) was substantially more antigenic and dramatically more immunogenic than in the N-terminal fusions. As anticipated, HBV core antigenicity and immunogenicity were greatly reduced in the internal fusion proteins. Replacement of an internal sequence of HBV core antigen (residues 78–82) with a fragment of HBV surface antigen containing the immunodominant a epitope also gave a product exhibiting positive HBV core antigenicity and immunogenicity [G. Borisova et al., "Hybrid Hepatitis B Virus Nucleocapsid Bearing an Immunodominant Region from Hepatitis B Surface Antigen", *J. Virol.*, 67, pp. 3696–3701 (1993)].

As a further alternative, or as an addition to the fusion proteins described above, immunogenic components may be attached to HBV core antigen by chemical cross-linking procedures.

Superimposition of the amino acid sequence of HBV core antigen on the physical structure suggested by Böttcher et al. (1997) helps to explain the low antigenicity of sequences fused at or near the carboxy terminus of HBV core antigen, since such sequences are likely to be buried within the HBV core antigen particles, while N-terminal fusions may benefit from flexible linker sequences, to bring the immunogen further from the relatively confined space at the foot of the spikes. Location of the immunodominant HBV core antigen epitope [residues 78–82; Salfeld et al. (1989)] at the tip of the spike shows the attraction of this position for insertion or attachment of the HBV capsid-binding peptide-immunogen. In principle, all these positions may be used simultaneously to increase the number and/or diversity of epitopes presented by a given HBV core antigen particle.

HBV Capsid-Binding Peptides Used to Ligate Immunogens to HBV Core Antigen Particles As described above, immunogens of interest may be linked to a HBV core particle using a ligand which is an HBV capsid-binding peptide. Such HBV capsid-binding peptides are isolated, purified peptides. These HBV capsid-binding peptides advantageously inhibit and interfere with HBV viral assembly by blocking the interaction between HBV core protein and HBV surface proteins.

Preferably, HBV capsid-binding peptides include peptides, fragments, analogs and homologs thereof, which are between about 2 and about 20 amino acids in length. More preferably, the peptides are between about 3 to about 15 amino acids in length. Such peptides include those listed in the tables below, as well as fragments and analogs thereof.

As used herein, the term "fragment" refers to an amino acid sequence which is shorter than the peptide from which it is derived, but which retains biological activity substantially similar to that of the original peptide. Such a fragment is at least two amino acids in length.

As used herein, the term "analog" refers to variations in the amino acid sequences of the peptides, which may typically include analogs that differ only by one to about four amino acid changes. Other examples of analogs include peptides with minor amino acid variations from the peptides exemplified herein. In particular, peptides containing conservative amino acid replacements, i.e., those that take place within a family of amino acids that are related in their side chains, constitute analogs.

Genetically encoded amino acids are generally divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan, and tyrosine are sometimes classified jointly as aromatic amino acids. With respect to HBV capsid-binding peptides, it may be beneficial to change one or more amino acids. Those of skill in the art may readily evaluate the impact of such a change.

The term "homolog" includes peptide fragments which share at least 60 percent identity at the amino acid level, and preferably 75 percent identity, and substantially similar biological activity to a reference peptide. These preferred percentages reflect the small size of the peptides.

Useful HBV capsid-binding peptides include those based on the peptides disclosed in *Dyson and Murray* (1995). Such peptides were synthesized following random mutagenesis of residues flanking the peptide LLGRMK (SEQ ID NO: 7) in the fusion phage B1 and re-selection against HBV core antigen in a bio-panning reaction to obtain derivatives that bind the antigen with improved affinity. High resolution electron cryomicroscopy demonstrated that such HBV capsid-binding peptides bind at the tips of the spikes of the HBV core protein shell. The inhibitory effect of the peptides on the interaction between HBV core antigen and HBV surface antigen proteins in infected cells was examined through transfection of permeabilized hepatoma Hep G2 cells with a replication-competent plasmid carrying a head-to-tail dimer of the HBV genome in the presence or absence of the peptide. See Böttcher et al. (1998).

HBV capsid-binding peptides carrying the LLGRNK (SEQ ID NO: 7) sequence reduced the yield of HBV in transfected hepatoma cell cultures in a dose-dependent manner and with relative efficiencies that reflect the $IC_{50}$ values for the peptides in their inhibition of reactions between HBV core antigen and L-HBV surface antigen in solution.

HBV capsid-binding peptides preferably have a half maximal concentration ($IC_{50}$) less than about 10, preferably less than 5, more preferably less than about 2, and most preferably less than about 0.5 μM. Preferred peptides include, but are not limited to: SLLGRMKG(β-A)C (SEQ ID NO: 8), RSLLGRMKGA (SEQ ID NO: 9), HRSLLGRMKGA (SEQ ID NO: 10), and RSLLGRMKGA (β-A)C (SEQ ID NO: 11), or peptides derived therefrom. Alternatively, such a peptide may be peptide ALLGRMKG (SEQ ID NO: 12), which inhibits the interaction between the long hepatitis B virus surface antigen (L HBsAg) and HBcAg, with a half maximal concentration ($IC_{50}$) of 10.0 μM.

HBV capsid-binding peptides are exemplified by the following, wherein $R_D^{Rel}$(nM) represents a relative dissociation constant for reactions between HBV core antigen and fd fusion phage carrying the peptide sequences in the amino terminal region of the gpIII protein:

| Sequence | $K_D^{Rel}$ (nM) |
|---|---|
| ADGALLGRMKGA (SEQ ID NO: 13) | 152 ± 5 |
| ADGALLGRMKPA (SEQ ID NO: 14) | 767 ± 8 |
| ADGSLLGRMKPA (SEQ ID NO: 15) | 322 ± 50 |
| ADGALLGRMKRA (SEQ ID NO: 16) | 181 ± 12 |
| ADGTLLGRMKLA (SEQ ID NO: 17) | 20 ± 2 |
| ADGSLLGRMKGA (SEQ ID NO: 18) | 1.7 ± 0.3 |
| ADRSLLGRMKGA (SEQ ID NO: 19) | 1.09 ± 0.02 |
| ADGSRSSLLGRMKGA (SEQ ID NO: 20) | 1.96 ± 0.32 |

-continued

| Sequence | $K_D^{Rel}$ (nM) |
|---|---|
| ADGAHSSLLGRMKGA (SEQ ID NO: 21) | 1.72 ± 0.17 |
| ADGHRSSLLGRMKGA (SEQ ID NO: 22) | 1.40 ± 0.13 |
| ADGPRSSLLGRMKGA (SEQ ID NO: 23) | 0.84 ± 0.07 |
| ADGAHRSLLGRMKGA (SEQ ID NO: 24) | 0.94 ± 0.12 |
| ADGYQRSLLGRMKGA (SEQ ID NO: 25) | 0.88 ± 0.08 |
| ADGTQRSLLGRMKGA (SEQ ID NO: 26) | 0.84 ± 0.06 |
| ADGMHRSLLGRMKGA (SEQ ID NO: 27) | 0.55 ± 0.03. |

These peptides, which mimic cytoplasmic regions of L HBsAg, were identified by selection from a random hexapeptide library displayed on filamentous phage and their affinities for HBV core antigen in solution determined in the phage associated form. The following related peptides (listed below), are also examples of HBV capsid-binding peptides and the $IC_{50}$ μM values represent the concentration of peptide required to inhibit binding of L HBsAg to HBV core antigen at a half maximal level, N/D represents no observable inhibition and β-A represents beta alanine:

| Sequence | $IC_{50}$ μM |
|---|---|
| ALLGRMKG (SEQ ID NO: 12) | 11.0 ± 0.8 |
| LLGRMKG (SEQ ID NO: 28) | 46.2 ± 7.4 |
| LGRMKG (SEQ ID NO: 29) | 980 ± 157 |
| GRMKG (SEQ ID NO: 30) | N/D |
| LLGRM (SEQ ID NO: 31) | N/D |
| CLLGRMKC (SEQ ID NO: 32) | 652 ± 74 |
| ALLPRMKG (SEQ ID NO: 33) | N/D |
| SLLGRMKG (SEQ ID NO: 34) | 6.4 ± 0.7 |
| SLLGRMK (SEQ ID NO: 35) | 40.7 ± 4.8 |
| SLLGRMKGA (SEQ ID NO: 6) | 2.4 ± 0.2 |
| GSLLGRMKGA (SEQ ID NO: 36) | 0.79 ± 0.23 |
| DGSLLGRMKGAA (SEQ ID NO: 37) | 3.0 ± 0.4 |

-continued

| Sequence | $IC_{50}$ μM |
|---|---|
| ADGSLLGRMKGAAG (SEQ ID NO: 38) | 4.5 ± 0.8 |
| ACSLLGRMKG (SEQ ID NO: 39) | 26.2 ± 5.0 |
| SLLGRMKG(β-A)C (SEQ ID NO: 8) | 1.8 ± 0.4 |
| RSLLGRMKGA (SEQ ID NO: 9) | 0.29 ± 0.02 |
| HRSLLGRMKGA (SEQ ID NO: 10) | 0.50 ± 0.04 |
| MHRSLLGRMKGA (SEQ ID NO: 40) | 0.80 ± 0.10 |
| RSLLGRMKGA(β-A)C (SEQ ID NO: 11) | 0.29 ± 0.03 |
| MHRSLLGRMKGAG(β-A)GC (SEQ ID NO: 41) | 3.80 ± 0.69. |

The HBV capsid-binding peptides, fragments, analogs and homologs thereof, which may serve as ligands to bind immunogens to HBV core antigen particles are preferably synthesized using conventional synthesis techniques, e.g., by chemical synthesis techniques. Alternatively, the skilled artisan may synthesize any of the peptides by using an automated peptide synthesizer using standard chemistry such as, for example, t-BOC chemistry. See, for example, L. A. Carpino, *J. Am. Chem. Soc*., 79, pp. 4427 (1957). And the peptides may be prepared by chemical cleavage of a protein or other methods. The peptides are isolated such that they are substantially free of chemical precursors or other chemicals when synthesized chemically, or obtained by chemical cleavage of a protein.

Alternatively, HBV capsid-binding peptides may be prepared by conventional genetic engineering techniques, e.g., recombinant DNA techniques in a host cell transformed with a nucleic acid sequence coding for the peptide, by cloning and expressing within a host microorganism or cell a DNA fragment carrying a coding sequence for the selected peptide. When produced by recombinant techniques, in appropriately transformed cells, the peptides may be purified from the cell culture medium, host cells, or both, using conventional methods. The recombinant peptides are isolated such that the peptide is substantially free of cellular material or culture medium when produced by recombinant DNA techniques. Coding sequences for the peptides may be prepared synthetically, or derived from viral RNA by known techniques, or from available cDNA-containing plasmids.

For use in the methods of this invention, the above-described peptides may be designed into conventionally known, or alternative constructs, to enhance production of the peptide, or its binding to HBV core antigen. For example, the peptides may be optionally fused to a protein or peptide fusion partner. Thus, one of skill in the art may design the peptide in association with a selected fusion partner, such as another peptide, or other peptides or proteins which impart desirable characteristics to it.

Systems for cloning and expressing HBV capsid-binding peptides in various microorganisms and cells, including, for example, *E. coli, bacillus, streptomyces, saccharomyces*, mammalian, yeast, insect cells and plant cells, and suitable vectors therefor, are known and available from private and public laboratories and depositories and from commercial vendors.

Whether produced recombinantly or synthesized, the HBV capsid-binding peptides may be purified using conventional purification means. One of skill in the art can readily determine the appropriate level of purity required for the desired application for which the peptides are to be used.

It should be understood that the choice of HBV capsid-binding peptide linker will depend, to some extent, on the nature of the particular HBV core antigen polypeptide forming the HBV core antigen particle. For example, HBV core antigen particles of different original virus strains may require different HBV capsid-binding peptide ligands, due to differing amino acid sequences at or near the ligand binding sites of the given HBV core antigen polypeptide.

Linkage of HBV Capsid-Binding Peptides to Immunogens

HBV capsid-binding peptides may be linked to immunogens of interest to form a capsid-binding immunogen through a peptide bond. Where the immunogen is itself a peptide, this will usually be achieved conveniently by a single synthesis, or by expression of a corresponding coding sequence, in transformed cells, of a peptide comprising the HBV capsid-binding sequence linked to the immunogen sequence, usually and preferably through two to five (and often three) glycine residues, to impart a degree of flexibility between the two components of this longer peptide. Alternatively, the peptides may be crosslinked to the immunogens.

The orientation of the linkage between the binding component of the peptide and immunogen may affect the efficiency of the ultimate process for crosslinking the capsid-binding immunogen to the HBV core antigen particle. Alternatively, among a number of capsid-binding immunogens to be crosslinked to an HBV core antigen particle, a given immunogen may be placed at the amino terminus of the peptide to which it is linked, while another immunogen may be placed at the carboxy terminus of the peptide to which it is linked. In some instances, it may be advantageous to place the same or different immunogens at each end of the HBV capsid-binding peptide. Such variation in organization of the HBV capsid-binding peptide-immunogen complexes to be crosslinked to a given HBV core antigen particle advantageously provides highly multicomponent or multivalent HBV core antigen particles. See FIG. 1.

Thus, orientation of the capsid-binding immunogen to be crosslinked to the HBV core antigen particle is important to the ultimate immunogenicity or multivalency of the resulting particle. Higher immunogenicity or multivalency are expected when the immunogen is oriented to the amino terminus of the HBV capsid-binding peptide. Such orientation, which affords greater flexibility, is also preferred for large size immunogens.

Linkage of Capsid-Binding Immunogens to the HBV Core Antigen Particle

Capsid-binding immunogens may be crosslinked to an HBV core antigen particle using any conventional crosslinking agent. Such crosslinking agents include, for example, multifunctional crosslinking agents, for example, glutaraldehyde, succinaldehyde, octanedialdehyde and glyoxol. Additional crosslinking agents are listed in the *Pierce Catalog and Handbook*, Pierce Chemical Company, Rockford, Ill. (1997). Other crosslinking agents include those such as 1-ethyl-3-(3-dimethylaminopropyl) carbodiimide hydrochloride (EDC) and N-hydroxysulphosuccinimide (sulpho-NHS), which link adjacent primary amino and carboxyl groups to form an amide bond. When added to a capsid-binding immunogen/HBV core antigen particle mixture, such agents covalently crosslink an available lysine component of the peptide to a neighboring aspartate or glutamate from HBV core antigen.

It should also be understood that the proportion of different immunogens attached to a given HBV core antigen particle may, of course, be varied by the relative proportions of respective immunogens in the mixture used for linking the capsid-binding immunogen to the HBV core antigen particle.

Therapeutic Compositions According to this Invention

The present invention also provides compositions useful for the therapeutic or prophylactic treatment of individuals with multicomponent or multivalent HBV core antigen particles disclosed herein. Any individual, including humans and other mammals, as well as any animals, may be treated with the HBV core antigen particles disclosed herein. Therapeutic compositions comprise a pharmaceutically effective amount of the HBV core antigen particles, i.e., an amount which is effective to immunize against one or more infectious agents or to treat one or more conditions in an individual to whom they are administered over some period of time. Prophylactic compositions comprise a prophylactically effective amount of the HBV core antigen particles, i.e., an amount which is effective to prevent one or more conditions in an individual to whom they are administered over some period of time.

In cases in which the HBV core antigen particles contain multiple immunogens of different types, compositions and vaccines comprising them may be used to elicit an enhanced immune response in an individual to each component immunogen. In cases in which the HBV core antigen particles contain multiple immunogens of a common type, compositions and vaccines comprising them may be used to elicit an enhanced immune response in an individual to the common immunogen. The latter compositions and vaccines are characterized by enhanced monovalency and potency, as compared with conventional monotherapies.

Compositions comprising multicomponent or multivalent HBV core antigen particles of the invention may be administered alone, or as part of a pharmaceutical or prophylactic preparation, with or without adjuvant, including controlled release formulations. They may additionally contain pharmaceutically acceptable carriers or diluents suitable for administration for the treatment of such infections. Suitable pharmaceutically acceptable carriers are physiologically inert and/or non-toxic. Numerous carriers are known in the art and may be chosen based upon the desired application. Exemplary carriers include, but are not limited to, sterile saline, lactose, sucrose, calcium phosphate, gelatin, dextrin, agar, alum, alumina, aluminum hydroxide, peptin, peanut oil, olive oil, sesame oil and water. Additionally, the carrier or diluent may include a time delay material, such as glycerol monosterate or glycerol disterate, alone, or in combination with a wax. In addition, conventional slow release polymer formulations including, for example, soluble glasses, may be used.

Potentially, compositions comprising multicomponent or multivalent HBV core antigen particles may contain other therapeutic or prophylactic agents. For example, such compositions may comprise a "cocktail" of multiple reagents useful in the treatment, or prevention, of infection. One such cocktail may include other reagents such as interferons, nucleoside analogs and/or N-acetyl-cysteine.

Optionally, compositions comprising immunogenic HBV core antigen particles may further contain immune system modifiers, such as adjuvants or cytokines which are useful to further induce antibody and T cell responses in the patient. Such modifiers include conventional alum based adjuvants, or muramyl dipeptides, preservatives, chemical stabilizers or other antigenic proteins. Typically, stabilizers, adjuvants and preservatives, etc., are optimized to determine the best formulation for efficacy in the desired application. Suitable preservatives may include chlorylbutynol, potassium sorbate, sorbic acid, sulfur dioxide, propyl gallade, parabens, glycerine and phenol.

Suitable amounts of these compositions may be determined based upon the level of response desired. In general, compositions comprising immunogenic HBV core antigen particles may contain between about 5 μg and about 200 μg of the particles. Such compositions may be administered as one or a series of inoculations, for example, three inoculations at intervals of two to six months. Suitable dosages may also be determined by judgment of the treating physician, taking into account factors, such as the patient's health status, weight or age, as well as the conventional dosage of a component immunogen, when administered as a monotherapy. Upon improvement of a patient's condition or likelihood of increase exposure to a given pathogen, a maintenance dose of a composition comprising immunogenic HBV core antigen particles may be administered, if necessary. Subsequently, the dosage or frequency of administration, or both, may be reduced to a level at which the desired effect is retained. At that point, treatment should cease. Individuals may, however, require intermittent treatment on a long-term basis upon recurrence of a given unwanted condition.

Compositions comprising multicomponent or multivalent HBV core antigen particles may be administered by any suitable route, such as, for example, parenteral administration, particularly intramuscular or subcutaneous, as well as oral administration. Other routes, may be used, such as pulmonary, nasal, aural, anal, dermal, ocular, intravenous, intraarterial, intraperitoneal, mucosal, sublingual, subcutaneous and intracranial.

Immunogenic HBV core antigen particles according to this invention may be used in the active therapy of HBV infected individuals to inhibit, decrease, or slow the proliferation of the virus within the body. Therapeutic compositions comprise the immunogenic HBV core antigen particles capable of disabling, inhibiting, or preventing the assembly mechanism of the virus. Such therapeutic compositions may be formulated to contain carriers or diluents, and one or more of the immunogenic HBV core antigen particles of the invention. Such carriers and diluents are discussed above in connection with certain other compositions, and are identifiable by those of skill in the art.

Preparation of compositions or vaccines which contain immunogenic HBV core antigen particles as active ingredients may be carried out to formulate injectable compositions or vaccines, either as liquid solutions or suspensions. Solid forms suitable for solution or suspension in liquid prior to injection may also be prepared. Preparations also may, in certain embodiments, be emulsified or encapsulated in liposomes, or in soluble glasses, for gradual release and/or prolonged delivery. Alternatively, preparations may be in aerosol or spray form. They may also be included in transdermal patches. The active ingredient may be mixed with any number of excipients which are pharmaceutically acceptable and compatible with the active ingredient or ingredients. Such excipients include, for example, Freund's incomplete, bacterial lipopolysaccharides, ion exchangers, alumina, aluminum stearate, muramyl dipeptide, lecithin, buffer substances, cellulose-based substances and polyethylene glycol.

Advantageously, vaccines comprising HBV core antigen particles according to this invention may be combination vaccines, comprising a number of different immunogens.

Such vaccines, include, for example, combination vaccines comprising immunogens against two or more of: diphtheria, tetanus, acellular pertussis, Haemophilus influenza, polio, measles, mumps, rubella, varicella, hepatitis B virus, hepatitis A virus or pneumococcal pneumonia. Other vaccines include those for inoculation of individuals prior to international travel. Such vaccines include, for example, vaccines comprising immunogens against two or more of: yellow fever, hepatitis B virus, hepatitis A virus, typhoid fever, meningococcal encephalitis or cholera.

Compositions comprising HBV core antigen particles according to this invention may also be used in immunotherapeutic regiments for desensitizing individuals to one or more allergens, such as animal allergens, insect allergens, plant allergens, atmospheric allergens and inhalant allergens.

According to an alternate embodiment of the present invention, HBV core antigen particles may be used to elicit antibodies against immunogens of interest, for use in immunotherapy or diagnostics. For example, antibodies raised in individuals inoculated with HBV core antigen particles may be isolated and used in purified form. Alternatively, such antibodies or B cells from the individual may be employed to produce monoclonal antibodies, using conventional techniques.

Detection Methods According to this Invention

The HBV core antigen particles of the present invention may also be used in number of conventional assay formats, particularly immunoassay formats for diagnosis of infection or exposure to infectious agents. Such utility is realized when the HBV capsid-binding peptide components of the constructs of the present invention are associated with a diagnostic label, a chemical marker, a toxin or another protein or peptide. For example, the HBV capsid-binding peptides may be associated with conventional labels which are capable, alone or in combination, with other compositions or compounds, of providing a detectable signal which would indicate the presence of a target analyte in a sample, upon exposure to the immunogen attached to a given HBV core antigen-binding peptide. Such detectable labels may be selected from among numerous compositions known and readily available to those skilled in the art of diagnostic assays.

The invention, therefore, is not limited by the selection of the particular assay format, and is believed to encompass assay formats that are known to those of skill in the art. For convenience, reagents for assays may be provided in the form of kits. These kits can include microtiter plates to which the HBV core antigen particles of this invention have been preadsorbed, various diluents and buffers, labeled conjugates for the detection of specifically bound capsid binding peptide immunogens and other signal generating reagents, such as enzyme substrates, cofactors and chromagens. Other components may be easily determined by those of skill in the art.

Alternatively, HBV core antigen particles according to this invention may be used in the immunological diagnostic tests currently available for pathogen detection, that is radioimmunoassay or ELISA (enzyme linked immunosorbent assay).

In one embodiment of the present invention, a sample to be tested for the presence of antibodies to various immunogens may be contacted with an HBV core antigen particle comprising detectably labelled HBV capsid binding immunogens having different immunogenic components, for a time sufficient to permit any antibodies in said sample to form a complex with one or more of the HBV capsid binding immunogens. Detection means may then be used the complex formed between the capsid binding immunogen(s) and said antibodies in said sample. A second screen may then be carried out on the sample based on each component immunogen, to identify the specificity of the antibodies in the sample.

In an alternate embodiment of this invention, a sample to be tested for the presence of antibodies to a specific immunogen may be contacted with an HBV core antigen particle comprising detectably labelled HBV capsid binding immunogens having that specific immunogen as their immunogenic component, for a time sufficient to permit any antibodies in said sample to form a complex with one or more of the HBV capsid binding immunogens. Due to the high valency of the specific immunogen demonstrated by the HBV core antigen particle, such a diagnostic assay is characterized by higher sensitivity than conventional assays.

EXAMPLES

In order that the invention described herein be more fully understood, the following examples are set forth. It should be understood that these examples are for illustrative purposes only and are not to be construed as limiting this invention in any manner.

Example 1

HBV Core Antigen Preparations

Expression of either HBV core antigen (aa3-183) or C-terminally truncated HBV core antigen aa3-148) in *E. coli* and purification were performed as described in *Dyson and Murray* (1995). Protein preparations were stored at 4° C. as sucrose gradient fractions in a buffer containing TBS, sucrose (20%) and $NaN_3$ (0.02%). Preparations were stable in this form for at least six months.

Chemical Cross Linking of HBV Capsid-Binding Peptides to HBV Core Antigen

The HBV capsid-binding peptide MHRSLLGRMKGA (SEQ ID NO: 40) (Albachem, University of Edinburgh) was crosslinked to HBV core antigen particles using 1-ethyl-3-(3-dimethylaminopropyl)carbodiimide hydrochloride (EDC) and N-hydroxysulphosuccinimide (sulpho-NHS) (both from Pierce Europe B.V.) These reagents link adjacent primary amino and carboxyl groups to form an amide bond. When added to an HBV capsid-binding peptide/HBV core antigen mixture, they should covalently crosslink the lysine from the peptide to a neighboring aspartate or glutamate from HBV core antigen, causing its molecular weight to increase.

More specifically, truncated HBV core antigen (15 μg) was incubated at room temperature in a buffer (30 μl) containing potassium phosphate (25 mM, pH7), NaCl (150 mM), (EDC 1.8 mM) and sulpho-NHS (1.8 mM) in the presence or absence of the peptide MHRSLLGRMKGA (SEQ ID NO: 40) (1 mM). After 18 h, the reaction was analyzed by SDS/PAGE (15% w/v) as described [Sambrook et al. (1989)]. Addition of EDC and sulpho-NHS to the peptide-HBV core antigen particle complex resulted in a band shift corresponding to about 0.1 kd, occurring on SDS-PAGE for a fraction of the HBV core antigen. Despite runs of the reaction under various conditions, no yield of more than 50% of the shifted protein band was obtained. This is consistent with one peptide binding to a dimer of HBV core antigen close to the local 2-fold axis and thus sterically blocking binding of another peptide to the 2-fold related site.

Example 2

HBV Core Antigen Preparations

In addition to the two HBV core antigen samples prepared in Example 1, samples of HBV core antigens with the HBV pre-S1 sequence 1–36 or the HBV surface antigen sequence 111–156 or 111–165 attached to the truncated HBV core antigen polypeptide (truncated at residue 144) via a short linker peptide sequence were also prepared as described by *Stahl and Murray* (1989).

Chemical Cross Linking of HBV Capsid-Binding Peptide to HBV Core Antigen

The following capsid-binding immunogens, made by solid phase synthesis, were obtained from Albachem, University of Edinburgh:

```
AS-151:    GSLLGRMKGA GGG LDPAFRG
           (SEQ ID NO: 42)

AS-152:    GSLLGRMKGA GGG EQKLISEEDL
           (SEQ ID NO: 43)

AS-163:    LDPAFR GG GSLLGRMKGA
           (SEQ ID NO: 44)

AS-164:    EQKLISEEDL GG GSLLGRMKGA,
           (SEQ ID NO: 45)
```

in which the sequence GSLLGRNKGA (SEQ ED NO: 36) is the HBV capsid-binding peptide, the sequence LDPAFR (SEQ ID NO: 46) is the HBV pre-S1 epitope or immunogen, and the sequence EQKLISEEDL (SEQ ID NO: 47) is the myc oncogene epitope or immunogen. These peptides, and the basic HBV capsid-binding peptide GSLLGRMKGA (SEQ ID NO: 36), were bound to an HBV core antigen particle separately, or in combination, at differing concentrations, and crosslinked with EDC or sulpho-NHS, as described in Example 1.

Properties of the Resulting HBV Core Antigen Particles

The products were analyzed by electrophoresis in acrylamide gels, in the presence of SDS (SDS-PAGE), followed by staining by Coomassie blue and Western blot analysis with monoclonal antibodies and polyclonal rabbit sera raised against HBV core antigen particles or denatured HBV surface antigen particles. Monoclonal antibodies to each of the HBV pre-S1 epitope and the myc oncogene epitope are available. These are, respectively, monoclonal antibody 18/7 [K. H. Heermann et al., *J. Virol*., 52, pp. 396–402 (1984)] and monoclonal antibody 9E10 [Invitrogen, Catalog # R950-25].

These experiments demonstrated that products from all the crosslinking reactions exhibited positive reactions with antibodies against each of the constituent epitopes in the ligation reaction components. Positive reactions were obtained with the immunogen linked through the amino or the carboxy terminus of the ligand peptide.

As detailed below, preparations of purified HBV core antigen particles from reactions involving crosslinking with two or more different immunogens, using a common HBV capsid-binding peptide ligand, react with antibodies to all the component immunogens. Furthermore, HBV core antigen particles precipitated with antibody specific for one of the immunogens exhibit cross-reactivity with antibodies to the other peptides(s) included in the ligand crosslinking procedure.

The products of the ligation were subjected to ultracentrifugation through sucrose gradients. They were precipitated with one of the antibodies, the anti-myc antibody, then analyzed by SDS-PAGE and Western blotting.

Material precipitated with one of the antibodies, for example, anti-myc antibody, showed strong cross-reactivity with both anti-myc and anti-pre-S1 antibody, in the Western blot. Products precipitated with the other antibody, the anti-pre-S1 antibody, also showed the same.

In reactions in which two HBV capsid-binding peptides, carrying different immunogens, were mixed in different proportions for binding and crosslinked to the core particles, analysis by SDS-PAGE and Western blotting showed that the relative intensities of staining with the two monoclonal antibodies reflected the proportion of the two immunogens in the mixture used for crosslinking.

These experiments showed that at least some of the HBV core particles resulting from the reactions had both immunogens covalently attached to them. Since the ligand peptide binds to the tips of the HBV core antigen particles (nucleocapsids), such preparations will display high immunogenic potency for both components and would be expected to elict high antibody titers in individuals to whom they are administered.

While we have hereinbefore presented a number of embodiments of this invention, it is apparent that our basic construction can be altered to provide other embodiments which utilize the process of this invention. Therefore, it will be appreciated that the scope of this invention is to be defined by the claims appended hereto rather than the specific embodiments which have been presented hereinbefore by way of example.

What is claimed is:

1. An HBV core antigen particle having multiple immunogen specificities comprising at least one capsid binding immunogen, said capsid binding immunogen comprising at least one HBV capsid-binding peptide component and at least one immungenic component, wherein said capsid binding immunogen comprises a diagnostic label or a chemical marker.

2. The HBV core antigen particle according to claim 1, wherein said capsid binding immunogen is linked to said particle through any amino acid residue of said HBV capsid-binding peptide component.

3. The HBV core antigen particle claim 1, wherein said capsid binding immunogen is linked to said particle through any amino acid residue or other residue of said immunogenic component.

4. The HBV core antigen particle according to claim 3, wherein said other residue of said immunogenic component is a carbohydrate.

5. The HBV core antigen particle according claim 1, wherein said capsid binding immunogen is crosslinked to said particle by a crosslinker.

6. The HBV core antigen particle according claim 1, wherein said immunogenic component is linked to said HBV capsid-binding peptide component directly or through a linker sequence.

7. The HBV core antigen particle according to claim 6, wherein said immunogenic component is linked to said HBV capsid-binding peptide component by a crosslinker.

8. The HBV core antigen particle according to claims 5 or 7, wherein said crosslinker is a multifunctional crosslinker.

9. The HBV core antigen particle according to claim 8, wherein said multifunctional crosslinker is selected from the group consisting of 1-ethyl-3-(3-dimethylaminopropyl) carbodimide hydrochloride and N-hydroxy-sulphosuccinimide.

10. The HBV core antigen particle according to claim 1, wherein said immunogenic component comprises one or more epitopes selected from the group consisting of immunologic epitopes, immunogenic epitopes and antigenic epitopes.

11. The HBV core antigen particle according to claim 10, wherein said epitopes are selected from the group consisting of linear epitopes, conformational epitopes, single epitopes and mixed epitopes.

12. The HBV core antigen particle according to claim 1, wherein said immunogenic component is selected from the group consisting of antigens, allergens, antigenic determinants, proteins, glycoproteins, antibodies, antibody fragments, peptides, peptide mimotopes which mimic an antigen or antigenic determinant, polypeptides, glycopeptides, carbohydrates, oligosaccharides, polysaccharides, oligonucleotides and polynucleotides.

13. The HBV core antigen particle according to claim 12, wherein said immunogenic component is selected from the group consisting of animal allergens, insect allergens, plant allergens, atmospheric allergens and inhalant allergens.

14. The HBV core antigen particle according to claim 1, wherein said immunogenic component is targeted to or derived from a pathogenic agent selected from the group consisting of viruses, parasites, mycobacteria, bacteria, bacilli, fungi, protozoa, plants, phage, animal cells and plant cells.

15. The HBV core antigen particle according to claim 14, wherein said virus is selected from the group consisting of retroviruses, herpesviruses, orthomyxoviruses, paramyxoviruses, hepadnaviruses, flaviviruses, picornaviruses, papoviviruses, adenoviruses, baculoviruses, hantaviruses, parvoviruses, enteroviruses, rhinoviruses, tumor viruses, DNA viruses, RNA viruses, togaviruses rhabdoviruses and poxviruses.

16. The HBV core antigen particle according to claim 15, wherein said virus is selected from the group consisting of human immunodeficiency type 1 virus, human immunodeficiency type 2 virus, T cell-leukemia virus, herpes simplex type 1 virus, herpes simplex type 2 virus, varicella-zoster virus, cytomegalovirus, Epstein-Barr virus, influenza A virus, influenza B virus, influenza C virus, respiratory syncytial virus, measles-like virus, mumps virus, parainfluenza virus, hepatitis B virus, hepatitis C virus, hepatitis A virus, hepatitis E virus, yellow fever virus, malaria, dengue virus, tick-borne encephalitis virus, oncovirus, poliomyelitis virus, papillomavirus, rubella virus, rabies virus and vaccinia virus.

17. The HBV core antigen particle according to claim 14, wherein said immunogenic component is targeted to or derived from bacillus, enterobacteria, clostridium, listeria, mycobacterium, pseudomonas, staphylococcus, eubacteria, mycoplasma, chlamydia, spirochetes, neisseria or salmonella.

18. The HBV core antigen particle according to claim 14, wherein said immunogenic component is targeted to diphtheria, tetanus, acellular pertussis, Haemophilus influenza, polio, measles, mumps, rubella, varicella, hepatitis B virus, hepatitis A virus, pneumococcal pneumonia, yellow fever, malaria, typhoid fever, meningococcal encephalitis or cholera.

19. A method for detecting the presence of antibodies to an immunogen in a sample comprising the steps of:

(a) contacting the sample with an HBV core antigen particle having multiple immunogen specificities according to claims 1, 14, 15, 17, or 18, for a time sufficient to permit any antibodies in said sample to form a complex with said capsid binding immunogen and;

(b) using detection means to detect the complex formed between the capsid binding immunogen and said antibodies in said sample.

20. The HBV core antigen particle according to claim 1, wherein said HBV core antigen is an HBV core antigen fusion protein.

21. The HBV core antigen particle according to claim 20, wherein said HBV core antigen fusion protein comprises an immunogenic epitope or an antigenic epitope.

22. The HBV core antigen particle according to claim 21, wherein said HBV core antigen fusion protein comprises an immunogenic epitope or an antigenic epitope fused to HBV core antigen directly or through a linker sequence.

23. The HBV core antigen particle according to claim 20, wherein said HBV core antigen fusion protein comprises truncated HBV core antigen.

24. The HBV core antigen particle according to claim 20, wherein said HBV core antigen fusion protein comprises HBV surface antigen or portions thereof.

25. The HBV core antigen particle according to claim 20, wherein said HBV core antigen fusion protein comprises a sequence selected from the group consisting of the pre-S1 region of HBV surface antigen, the pre-S2 region of HBV surface antigen, the immunodominant a region of HBV surface antigen and portions thereof.

26. The HBV core antigen particle according to claim 1, wherein said HBV core antigen is a full length HBV core antigen polypeptide, or portions, truncations, mutations or derivatives thereof which are capable of assembling in particulate form.

27. The HBV core antigen particle according to claim 1, wherein said HBV capsid-binding peptide component is selected from the group consisting of SLLGRMKGA (SEQ ID NO:6), GSLLGRMKGA (SEQ ID NO: 36) DGSLLGRMKGAA (SEQ ID NO: 37), ADTGSLLGRMKGAAG (SEQ ID NO: 38) SLLGRMKG(β–A)C (SEQ ID NO: 8), RSLLGRMKGA (SEQ ID NO: 9), HRSLLGRMKGA (SEQ ID NO: 10), ALLGRMKG (SEQ ID NO: 12), MHRSLLGRMKGA (SEQ ID NO: 40), RSLLGRMKGA(β–A)C (SEQ ID NO: 11) and MHRSLLGRMKGAG(β–A)GC (SEQ ID NO: 41).

28. The HBV core antigen particle according to claim 1, wherein said HBV capsid binding component is a fragment or analog of a peptide selected from the group consisting of: SLLGRMKGA (SEQ ID NO: 6), GSLLGRMKGA (SEQ ID NO: 36), DGSLLGRKGAA (SEQ ID NO: 37), ADGSLLGRMKGAAG (SEQ ID NO: 38), SLLGRMKG (β–A)C (SEQ ID NO: 8), RSLLGRMKGA (SEQ ID NO: 9), HRSLLGRMKGA (SEQ ID NO: 10), ALLGRMKG (SEQ ID NO: 12), MHRSLLGRMKGA (SEQ ID NO: 40), RSLLGRMKGA(β–A)C (SEQ ID NO: 11)and MHRSLLGRMKGAG(β–A)GC (SEQ ID NO: 41).

* * * * *

SEQUENCE LISTING

```
<160> NUMBER OF SEQ ID NOS: 47

<210> SEQ ID NO 1
<211> LENGTH: 9
<212> TYPE: PRT
<213> ORGANISM: Human immunodeficiency virus

<400> SEQUENCE: 1

Gly Glu Leu Asp Arg Trp Glu Lys Ile
  1               5


<210> SEQ ID NO 2
<211> LENGTH: 7
```

-continued

```
<212> TYPE: PRT
<213> ORGANISM: Human immunodeficiency virus

<400> SEQUENCE: 2

Glu Leu Asp Lys Trp Ala Ser
  1               5


<210> SEQ ID NO 3
<211> LENGTH: 12
<212> TYPE: PRT
<213> ORGANISM: Human immunodeficiency virus

<400> SEQUENCE: 3

Ile Gly Pro Gly Arg Ala Phe Tyr Thr Thr Lys Asn
  1               5                  10


<210> SEQ ID NO 4
<211> LENGTH: 6
<212> TYPE: PRT
<213> ORGANISM: Human immunodeficiency virus

<400> SEQUENCE: 4

Glu Leu Asp Lys Trp Ala
  1               5


<210> SEQ ID NO 5
<211> LENGTH: 9
<212> TYPE: PRT
<213> ORGANISM: Human immunodeficiency virus

<400> SEQUENCE: 5

Asp Arg Phe Tyr Lys Thr Leu Arg Ala
  1               5


<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:HBV capsid
      binding peptide

<400> SEQUENCE: 6

Ser Leu Leu Gly Arg Met Lys Gly Ala
  1               5


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:HBV capsid
      binding peptide

<400> SEQUENCE: 7

Leu Leu Gly Arg Met Lys
  1               5


<210> SEQ ID NO 8
<211> LENGTH: 10
<212> TYPE: PRT
<213> ORGANISM: Artificial Sequence
<220> FEATURE:
<221> NAME/KEY: MOD_RES
<222> LOCATION: (9)
<223> OTHER INFORMATION: bAla
<220> FEATURE:
```

-continued

```
<223> OTHER INFORMATION: Description of Artificial Sequence:HBV
      capsid-binding peptide

<400> SEQUENCE: 8

Ser Leu Leu Gly Arg Met Lys Gly Xaa Cys
  1               5                   10


<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 9

Arg Ser Leu Leu Gly Arg Met Lys Gly Ala
  1               5                   10


<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 10

His Arg Ser Leu Leu Gly Arg Met Lys Gly Ala
  1               5                   10


<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide
<220> FEATURE:
<221> NAME/KEY: MOD_RES
<222> LOCATION: (11)
<223> OTHER INFORMATION: bAla

<400> SEQUENCE: 11

Arg Ser Leu Leu Gly Arg Met Lys Gly Ala Xaa Cys
  1               5                   10


<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 12

Ala Leu Leu Gly Arg Met Lys Gly
  1               5


<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 13
```

-continued

```
Ala Asp Gly Ala Leu Leu Gly Arg Met Lys Gly Ala
  1               5                  10


<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 14

Ala Asp Gly Ala Leu Leu Gly Arg Met Lys Pro Ala
  1               5                  10


<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 15

Ala Asp Gly Ser Leu Leu Gly Arg Met Lys Pro Ala
  1               5                  10


<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 16

Ala Asp Gly Ala Leu Leu Gly Arg Met Lys Arg Ala
  1               5                  10


<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 17

Ala Asp Gly Thr Leu Leu Gly Arg Met Lys Leu Ala
  1               5                  10


<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 18

Ala Asp Gly Ser Leu Leu Gly Arg Met Lys Gly Ala
  1               5                  10


<210> SEQ ID NO 19
<211> LENGTH: 12
<212> TYPE: PRT
<213> ORGANISM: Artificial Sequence
<220> FEATURE:
```

-continued

```
<223> OTHER INFORMATION: Description of Artificial Sequence:HBV
      capsid-binding peptide

<400> SEQUENCE: 19

Ala Asp Arg Ser Leu Leu Gly Arg Met Lys Gly Ala
  1               5                  10


<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 20

Ala Asp Gly Ser Arg Ser Ser Leu Leu Gly Arg Met Lys Gly Ala
  1               5                  10                  15


<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 21

Ala Asp Gly Ala His Ser Ser Leu Leu Gly Arg Met Lys Gly Ala
  1               5                  10                  15


<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 22

Ala Asp Gly His Arg Ser Ser Leu Leu Gly Arg Met Lys Gly Ala
  1               5                  10                  15


<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 23

Ala Asp Gly Pro Arg Ser Ser Leu Leu Gly Arg Met Lys Gly Ala
  1               5                  10                  15


<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 24

Ala Asp Gly Ala His Arg Ser Leu Leu Gly Arg Met Lys Gly Ala
  1               5                  10                  15
```

-continued

```
<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 25

Ala Asp Gly Tyr Gln Arg Ser Leu Leu Gly Arg Met Lys Gly Ala
  1               5                  10                  15


<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 26

Ala Asp Gly Thr Gln Arg Ser Leu Leu Gly Arg Met Lys Gly Ala
  1               5                  10                  15


<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 27

Ala Asp Gly Met His Arg Ser Leu Leu Gly Arg Met Lys Gly Ala
  1               5                  10                  15


<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 28

Leu Leu Gly Arg Met Lys Gly
  1               5


<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 29

Leu Gly Arg Met Lys Gly
  1               5


<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 30
```

-continued

```
Gly Arg Met Lys Gly
  1               5


<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 31

Leu Leu Gly Arg Met
  1               5


<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 32

Cys Leu Leu Gly Arg Met Lys Cys
  1               5


<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 33

Ala Leu Leu Pro Arg Met Lys Gly
  1               5


<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 34

Ser Leu Leu Gly Arg Met Lys Gly
  1               5


<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 35

Ser Leu Leu Gly Arg Met Lys
  1               5


<210> SEQ ID NO 36
<211> LENGTH: 10
<212> TYPE: PRT
<213> ORGANISM: Artificial Sequence
```

```
<220> FEATURE:
<223> OTHER INFORMATION: Description of Artificial Sequence:HBV
      capsid-binding peptide

<400> SEQUENCE: 36

Gly Ser Leu Leu Gly Arg Met Lys Gly Ala
  1               5                  10


<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 37

Asp Gly Ser Leu Leu Gly Arg Met Lys Gly Ala Ala
  1               5                  10


<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 38

Ala Asp Gly Ser Leu Leu Gly Arg Met Lys Gly Ala Ala Gly
  1               5                  10


<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 39

Ala Cys Ser Leu Leu Gly Arg Met Lys Gly
  1               5                  10


<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 40

Met His Arg Ser Leu Leu Gly Arg Met Lys Gly Ala
  1               5                  10


<210> SEQ ID NO 41
<211> LENGTH: 16
<212> TYPE: PRT
<213> ORGANISM: Artificial Sequence
<220> FEATURE:
<221> NAME/KEY: MOD_RES
<222> LOCATION: (14)
<223> OTHER INFORMATION: bAla
<220> FEATURE:
<223> OTHER INFORMATION: Description of Artificial Sequence:HBV
      capsid-binding peptide

<400> SEQUENCE: 41
```

-continued

```
Met His Arg Ser Leu Leu Gly Arg Met Lys Gly Ala Gly Xaa Gly Cys
  1               5                  10                  15


<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 42

Gly Ser Leu Leu Gly Arg Met Lys Gly Ala Gly Gly Gly Leu Asp Pro
  1               5                  10                  15

Ala Phe Arg Gly
             20


<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 43

Gly Ser Leu Leu Gly Arg Met Lys Gly Ala Gly Gly Gly Glu Gln Lys
  1               5                  10                  15

Leu Ile Ser Glu Glu Asp Leu
             20


<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence:HBV
      capsid-binding peptide

<400> SEQUENCE: 44

Leu Asp Pro Ala Phe Arg Gly Gly Gly Ser Leu Leu Gly Arg Met Lys
  1               5                  10                  15

Gly Ala


<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence:myc oncogene
      epitope or immunogen

<400> SEQUENCE: 45

Glu Gln Lys Leu Ile Ser Glu Glu Asp Leu Gly Gly Gly Ser Leu Leu
  1               5                  10                  15

Gly Arg Met Lys Gly Ala
             20


<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:HBV pre-S1
      epitope or immunogen
```

-continued

```
<400> SEQUENCE: 46

Leu Asp Pro Ala Phe Arg
  1               5


<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence:myc oncogene
      epitope or immunogen

<400> SEQUENCE: 47

Glu Gln Lys Leu Ile Ser Glu Glu Asp Leu
  1               5                  10
```